United States Patent [19]

Safai et al.

[11] Patent Number: 4,649,115

[45] Date of Patent: Mar. 10, 1987

[54] MONOCLONAL ANTIBODIES TO SKIN CELLS

[75] Inventors: Bijan Safai; Edward A. Boyse, both of New York, N.Y.; Fung-Win Shen, Parsippany, N.J.

[73] Assignee: Sloan-Kettering Institute, New York, N.Y.

[21] Appl. No.: 480,717

[22] Filed: Mar. 31, 1983

[51] Int. Cl.$^4$ ............ G01N 33/54; C12N 5/00; C12N 15/00; C12R 1/91
[52] U.S. Cl. ............... 435/240; 436/548; 435/68; 435/172.2; 435/948; 935/104
[58] Field of Search ............ 435/68, 172.2, 240, 435/241, 948, 548; 935/104, 110

[56] References Cited

PUBLICATIONS

Gigi et al., "Detection of a Cytokeratin Determinant Common to Diverse Epithelial Cells by a Broadly Cross-Reacting Monoclonal", EMBO Journal 1(11) pp. 1429–1437 (1982).

Eichner et al., "Expression of Keratin Antigens During Normal Epidermal Differentiation: Monoclonal Antibodies Studies", Journal of Investigative Dermatology 78(4) p. 341 (1982).

Grimm et al., "Hybridoma Antibodies to A431 Cell Plasma Membranes: Tests for Specific Immunoprecipitation of EGF Receptors", Monoclonal Antibodies in Endocrine Research ed. Fellows et al., Raven Press NY, pp. 99–110 (1981).

Woodcock-Mitchell et al., "Immunolocalization of Keratin Polypeptides in Human Epidermis Using Monoclonal Antibodies", Journal of Cell Biology 95 pp. 580–588 (1982).

Primary Examiner—Charles F. Warren
Assistant Examiner—John Tarcza
Attorney, Agent, or Firm—Felfe & Lynch

[57] ABSTRACT

Successive layers of guinea pig epidermis display discrete antigenic markers that are recognized by a selected panel of five monoclonal antibodies produced by hybridomas resulting from immunization of mice with suspensions of dissociated viable guinea pig epidermal cells. Antigen to Gpsk-1 marks the basement membrane, which membrane is probably produced by basal cells. Antigen to Gpsk-2 is expressed by basal and suprabasal cells. Antigens to both Gpsk-3 and Gpsk-4 occur on the spinous and overlying layers but are distinguished by differences in their representation on certain non-epidermal cell types and on other epithelia. Antigen to Gpsk-5 is found on basement membrane and on spinous and overlying granular and horny cells. Antigens to Gpsk-2 through 5 are situated at the cell surface and may recognize integral plasma membrane molecules expressed in differentiative sequence. The five antibodies differ also in their antigenic marker distribution among epithelial as well as other selected tissue types. These findings provide a background to potential dermatological applications of monoclonal antibodies to human epidermis.

4 Claims, No Drawings

MONOCLONAL ANTIBODIES TO SKIN CELLS

This invention relates to preparation of mouse monoclonal antibodies to guinea pig skin cells. Different epidermal cell layers exhibit certain of the antigens related to said antibodies. These antigens then serve as markers for keratinocytes in the basement, spinous (prickle), granular and horny layers of epidermis. The monoclonal antibodies can be used to assay for the different types of keratinocytes in epidermis. A method of phenotyping epidermal keratinocytes is presented.

BACKGROUND

Mapping of cell-surface antigens is of great importance in medicine. Histocompatability antigen mapping reveals which donors of organs, or tissues such as blood, are most likely to be rejected or accepted by needful recipients of the same species. Tissue cells of donor and recipient must be well matched with respect to the different sets of cell surface antigens specific to the tissue to be transferred or transplanted. Matching helps to avoid foreign tissue rejection by the immune system, which functions to remove invasive cells i.e. those cells which do not originate from the selected recipient, and are often depicted as "non-self".

Such mapping is also of medical value in autoimmune disease, in which the organism rejects its own cells as if foreign, by immune reaction of auto antibodies against cells which are "self", i.e. they do originate from the selected recipient, but are not recognized as self. Rheumatic fever, Rheumatoid arthritis, Lupus Erythematosis are some examples of such disorders.

Mapping of cell antigens is useful in diagnosing and identifying normal differentiation antigens as well as antigens associated with various diseases.

The introduction by Köhler and Milstein in 1975 of a revolutionary new procedure for the routine production of monoclonal antibodies using hybridomas allows the production of almost unlimited quantities of antibodies of precise and reproducible specificity. While conventional antisera produced by immunizing animals with tumor cells or other antigens contain a myriad of antibodies differing in their specificity and properties, hybridomas produce a single antibody with uniform characteristics. The Köhler-Milstein procedure entails the fusion of spleen cells from an immunized animal with an immortal myeloma cell line. From the fused cells (hybridomas), clones are selected that produce antibody of the desired specificity (monoclonal antibody or mAb). As hybridoma cells can be cultured indefinitely (or stored frozen in liquid nitrogen), a constant supply of antibody is assured.

Antibodies are proteins that have the ability to combine with and recognize other molecules, known as antigens. Monoclonal antibodies are no different from other antibodies except that they are completely uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are markers by which the cell is identified.

These antigenic markers can be used to observe the normal process of cell differentiation and to locate abnormalities within a given cell system. The process of differentiation is accompanied by changes in the cell surface antigenic phenotype. Antigens that distinguish cells belonging to distinct differentiation lineages, or distinguish cells at different phases in the same differentiation lineage, can be observed if the correct antibody is available. Initial recognition of differentiation antigens came about through analysis of surface antigens of T-cell leukemias of the mouse and the description of the TL, Thy-1, and Lyt series of antigens. [Edward A. Boyse, Lloyd J. Old, Annual Review of Genetics 3,269–290, 1969]. The analysis of these T-cell differentiation antigens was greatly simplified by the availability of normal T cells and B cells of mouse and man and is relatively advanced, but less is known about differentiation antigens displayed on normal and neoplastic cells belonging to other lineages.

The hybridoma technology is exceptionally useful to determine cell surface composition i.e. cell surface phenotype. Preparation of a series of these hybridomas facilitates cell surface phenotype mapping since each hybridoma secrets its own monoclonal antibody specific for a tissue antigen. Groups of these can be prepared specific for any tissue or part thereof, by immunization with the cells or antigenic components of said tissue. A broad spectrum tissue antigen such as whole cells should produce an array of monoclonal antibodies. In the present work epidermal cell surface antigens are mapped. Identification of cell surface antigens and/or subclasses of cells such as keratinocytes is important for future diagnosis and treatment of diseases of epidermis.

SUMMARY

Keratinocyte cell suspensions composed of the serial layers of the guinea pig epidermis are used to inoculate female mice. The resulting mouse spleen cells are fused with mouse myeloma cells. Supernatants are tested for reactivity with guinea pig epidermal cell suspensions in the $^{125}$I-Protein A binding assay. Five different positive clones, Gpsk-1, Gpsk-2, Gpsk-3, Gpsk-4 and Gpsk-5 are found.

Guinea pig epidermis, certain epithelia and other tissues, serve as loci for the antigens recognized by these clones. The panel of antibodies serves to differentiate keratinocytes from the four different epidermal layers. These cell markers recognize antigen characteristics for the different keratinocytes of the epidermis. Thus for the first time sub-sets of keratinocytes have been identified by a panel of monoclonal antibodies. These antigen locations serve as a starting point for new diagnostic criteria and for treatment of epidermal diseases. They are also used to assay for the different types of keratinocytes found throughout the epidermis.

DESCRIPTION

The following is a detailed description of the preferred embodiment of the invention.

Body skin is obtained from Meon-chase female guinea pigs. A Davol/Simon dermatome is used to obtain split-thickness sections thereof. These sections are incubated with the dermis side in contact with a layer of 0.25% typsin (purified, Millepore Corp.) in phosphate buffered saline for 90 min. at 37° C. and pH 7.8. This separates epidermis from dermis. The separated epidermis is stirred for 10 min. and epidermal cells released thereby are twice washed with Hanks balanced salt solution containing penicillin and streptomycin. Suspensions of these released guinea pig epidermal cells in the aforesaid salt and antibiotic solution are used both for immunization as well as for serological testing analysis of mammal epidermal cells.

The vast majority of cells in the epidermal suspensions are keratinocytes from the serial layers of the epidermis: basal, spinous (prickle), granular and horny. The layers are also referred to as stratum germinativum, stratum granulosum and stratum corneum. In the stratum germinativum, the basal and spinous cells make up the stratum cylindricum and stratum spinosum respectively. The granular and horny cells are found in the stratum granulosum and stratum corneum respectively. Epidermis is separated from dermis tissue by a basement membrane on which the basal cells rest. Spinous cells are the next overlying epidermal cell layer and these merge into granular cells which become progressively more flattened and keratinized to form the outermost horny layer. A small number of melanocytes and Langerhans cells are present as well. Tests with trypan blue show that greater than 75% of the prepared suspended epidermal cells are viable. This viability is maintained by the use of ice-bath temperatures for the suspensions. Control preparations of human and mouse epidermal cells are made in the same manner from surgical material and tail skin respectively.

The guinea pig epidermal cell suspensions are used to inoculate mammals, and in a preferred embodiment BALB/c female mice age 8–10 weeks. Seven intraperitoneal inoculations are done at intervals of 1–3 weeks. Each inoculation contains $20\text{--}40 \times 10^6$ cells. There is a final intravenous injection of the same number of cells. Three days after this final injection, mouse spleen cells are removed and fused with non-secreting P/NSI/1 mouse myeloma cells in a ratio of 2 spleen cells to 1 myeloma cell in polyethylene glycol.

The $I^{125}$-Protein A (PA) binding assay is used to screen supernatants of the fusion process for antibody reaction with the above guinea pig epidermal cell suspensions which also serve as antigen. Five different positive hybridoma clones are isolated and passed in vivo in mice. These hybridomas produce antibodies for guinea pig keratinocyte cell antigenic markers. These antibodies are Gpsk-1, Gpsk-2, Gpsk-3, Gpsk-4 and Gpsk-5.

These five antibodies have titers of 1:1000 to 1:8000 with the aforesaid guinea pig epidermal cell suspension. There are no positive reactions with mouse or human epidermal cells. All activity in the $^{125}$I-PA assay can be removed by absorption of 0.1 ml of a 1:1000 dilution of the test sample with $5 \times 10^6$ guinea pig epidermal cells. Similar absorption with $2 \times 10^7$ mouse epidermal cells shows no significant loss of activity in those samples giving positive response in the $^{125}$I-PA assay.

Non-epidermal cells are tested for antigen by absorbing 0.1 ml of stock monoclonal antibody (1:1000 dilution) with equal volumes of guinea pig packed cells or tissue homogenates in the $^{125}$I-PA assay. Positive absorptions are verified using the same mouse tissue wherein no absorption is detected as a control. Tissue sections are tested for antigen by indirect immunofluorescence as follows: 4 tissue sections (cryotome) of the guinea pig or human skin or other tissues are incubated with mouse ascites fluid monoclonal antibody at various dilutions at room temperature for 30 min. to test for antigen. Sections are further then washed and reacted with 1:20 fluoresceinated goat anti-mouse Ig(Cappel) for 30 min. Sections are washed and mounted in glycine. The results show differentiation of keratinocyte cells within different epidermal layers. Specifically, Gpsk-1 markers are found in the basement membrane whereas Gpsk-2 markers are found in the basal and suprabasal cell layers. Gpsk-3 and Gpsk-4 markers both occur on the spinous and overlying layers. These last two markers differ, however, in their location on other epithelial cells as well as on selected non-epidermal cell types. Gpsk-5 markers are found on basement membrane and on spinous, granular and horny cells. Gpsk-1, 3, 4 and 5 antibodies belong to immunoglobulin subclass $IgG_1K$, whereas Gpsk-2 belongs to $IgG_2K$.

Table I summarizes the locations of antigenic markers in certain selected guinea pig tissues for this monoclonal antibody panel of five. $^{125}$I absorption is described above. IIF is indirect immunofluorescence as described above and + indicates a positive reaction whereas − indicates no reaction.

Previous work on skin cell markers of the mouse has described Skn-1 and Skn-2 epidermal antigens of mouse skin, defined by alloantibody produced from mouse vs. mouse skin grafts (Edward A. Boyse et al, *Nature*, v. 227, 901–903 (August 29, 1970). Stephen S. Wachtel et al, *Immunogenetics*, 5:17–23, 1977). The present work concerns Gpsk antigens as identified by xenoantibody from mouse vs. guinea pig skin cell injections. These Gpsk antigens are more likely to be common to the guinea pig species and not to show genetic variation within the species, as do the skin mouse alloantibodies in the mouse. The detailed description of the invention as applied to guinea pig epidermal cells is for illustrative purposes only and is not meant to limit the invention. Although only five hybridomas producing monoclonal antibody against epidermal cell antigens are described, it is contemplated that the present invention encompasses all monoclonal antibodies exhibiting the characteristics described herein.

Indeed epidermal cells of other species can be used to elicit such antibodies. An obvious goal is to use human epidermal cells to elicit antibodies to diagnose and treat human epidermal diseases such as pemphigus.

The following hybridoma lines are maintained on deposit at Sloan-Kettering Institute for Cancer Research, 1275 York Avenue, New York, N.Y. 10021 under designations corresponding to the monoclonal antibody produced by each hybridoma as follows:

Gpsk-1
Gpsk-2
Gpsk-3
Gpsk-4
Gpsk-5

Said hybridoma lines have been deposited on Feb. 28, 1983 with American Type Culture Collection, 1230 Parklawn Dr., Rockville, Md. 20852 under ATCC designations corresponding to the above Sloan-Kettering designations as follows:

| SKI # | ATCC ACCESSION # |
| --- | --- |
| Gpsk-1 | HB 8218 |
| Gpsk-2 | HB 8281 |
| Gpsk-3 | HB 8282 |
| Gpsk-4 | HB 8283 |
| Gpsk-5 | HB 8284 |

TABLE I

| Material | Preparation | Tests | Gpsk-1 | Gpsk-2 | Gpsk-3 | Gpsk-4 | Gpsk-5 |
|---|---|---|---|---|---|---|---|
| Antigenic Markers for Gpsk mAbs | | | | | | | |
| Epidermis | free cells | 125$_I$ | + | + | + | + | + |
| | | absorption | + | + | + | + | + |
| | sections | IIF | + | + | + | + | + |
| Esophageal epithelium | sections | IIF | + | + | + | − | − |
| Vaginal epithelium | sections | IIF | + | − | + | − | − |
| Small intestine epithelium | sections | IIF | − | − | − | − | − |
| Spleen | free cells | 125$_I$ | − | − | − | − | − |
| | | absorption | − | − | − | + | − |
| | sections | IIF | − | − | − | − | − |
| Bone marrow | free cells | 125$_I$ | − | − | − | − | − |
| | | absorption | − | − | − | + | − |
| Blood | free cells | 125$_I$ | − | − | − | − | − |
| | | absorption | − | − | − | − | − |
| Liver | homogenates | absorption | − | + | + | + | − |
| | section | IIF | − | + | − | + | − |
| Kidney | homogenates | absorption | − | + | − | + | − |
| | section | IIF | − | + | − | − | − |
| Brain | homogenates | absorption | − | − | − | − | − |
| Dilutions used for IIF | | | | | | | |
| Highest Titer | | | 1:1024 | 1:128 | 1:1024 | 1:256 | 1:1024 |

IIF = Indirect immunofluorescence
125$_I$ = radioactive iodine - PA immunoassay

What we claim is:

1. Hybridoma cell lines producing monoclonal antibody immunologically binding to and subsetting normal guinea pig keratinocyte cell antigen from the four different epidermal cell layers wherein the monoclonal antibodies are selected from the group consisting of Gpsk-1 (HB 8218), Gpsk-2, (HB 8281), Gpsk-3 (HB 8282), Gpsk-4 (HB 8283) and Gpsk-5 (HB 8284) and wherein
   (1) Gpsk-1 and Gpsk-5 bind epidermal basement membrane keratinocyte antigen,
   (2) Gpsk 2 binds epidermal basal and suprabasal layer keratinocyte antigen,
   (3) Gpsk 3 and Gpsk 4 bind epidermal spinous and overlaying layer keratinocyte antigen, and
   (4) Gpsk 5 binds epidermal spinous, granular and horny cell layer keratinocyte antigen.

2. Monoclonal antibodies immunologically binding to and subsetting normal guinea pig keratinocyte cell antigen from the four different epidermal cell layers wherein the monclonal antibodies are selected from the group consisting of Gpsk-1 produced by cell line HB 8218, Gpsk-2 produced by cell line HB 8281, Gpsk-3 produced by cell line HB 8282, Gpsk-4 produced by cell line HB 8283 and Gpsk 5 produced by cell line 8284, wherein
   (1) Gpsk-1 and Gpsk-5 bind epidermal basement membrane keratinocyte antigen,
   (2) Gpsk 2 binds epidermal basal and suprabasal layer keratinocyte antigen,
   (3) Gpsk 3 and Gpsk 4 bind epidermal spinous and overlaying layer keratinocyte antigen, and
   (4) Gpsk 5 binds epidermal spinous, granular and horny cell layer keratinocyte antigen.

3. Hybridoma cell lines producing monoclonal antibody selected from the group consisting of Gpsk-1 (HB8218), Gpsk-2 (HB-8281), Gpsk-3 (HB 8282), Gpsk-4 (HB8283), Gpsk-5 (HB 8284) wherein said monoclonal antibody binds and subsets normal guinea pig keratinocyte cell antigen from the four different epidermal layers and wherein the hybridoma is produced by a cell fusion process which comprises:
   (a) immunization of a mammal with guinea pig epidermal cells;
   (b) extraction of the spleen cells of said mammal;
   (c) fusion of said spleen cells with a myeloma-derived cell line.

4. Method for immunologically distinguishing epidermal keratinocyte cells and subsets thereof from other epidermal cells which comprises:
   (a) contacting said cells with monoclonal antibody selected from the group consisting of Gpsk 1 (HB 8218), Gpsk 2 (HB 8281), Gpsk 3 (HB 8282), Gpsk 4 (HB 8283) and Gpsk 5 (HB 8284) immunologically binding keratinocyte antigen wherein the monoclonal antibody is produced by a hybridoma cell line formed by fusing a myeloma derived cell line with splenocytes derived from a mammal immunized with guinea pig epidermal cells; and
   (b) detecting immunological binding between keratinocyte antigens and said antibody, wherein Gpsk-1 and Gpsk-5 bind epidermal basement membrane keratinocyte antigen, Gpsk 2 binds epidermal basal and suprabasal layer keratinocyte antigen, Gpsk 3 and 4 bind epidermal spinous and overlaying layer keratinocyte antigen, and Gpsk 5 bind epidermal spinous, granular and horny cell layer keratinocyte antigen.

* * * * *